(12) United States Patent
Kamiya

(10) Patent No.: US 8,177,357 B2
(45) Date of Patent: May 15, 2012

(54) METHOD AND DEVICE FOR ADJUSTING LUMINANCE OF LIGHT TRANSMITTED THROUGH GLASSES

(75) Inventor: Hiroshi Kamiya, Tokyo (JP)

(73) Assignee: NEC Corporation, Tokyo (JP)

(*) Notice: Subject to any disclaimer, the term of this patent is extended or adjusted under 35 U.S.C. 154(b) by 414 days.

(21) Appl. No.: 12/559,587

(22) Filed: Sep. 15, 2009

(65) Prior Publication Data
US 2010/0066971 A1 Mar. 18, 2010

(30) Foreign Application Priority Data
Sep. 17, 2008 (JP) ............... P2008-238257

(51) Int. Cl.
G02C 7/12 (2006.01)
(52) U.S. Cl. .......................... 351/49; 351/158
(58) Field of Classification Search .................. 351/49, 351/158, 163, 177
See application file for complete search history.

(56) References Cited

U.S. PATENT DOCUMENTS 5,552,841 A * 9/1996 Gallorini et al. ............. 351/49
5,654,786 A * 8/1997 Bylander ..................... 351/49
5,790,225 A * 8/1998 Flados ......................... 351/49
5,841,507 A * 11/1998 Barnes ......................... 351/49

FOREIGN PATENT DOCUMENTS

| JP | 9-015542 A | 1/1997 |
|---|---|---|
| JP | 9-127464 A | 5/1997 |
| JP | 2003275317 A | 9/2003 |
| JP | 2008076767 A | 4/2008 |

OTHER PUBLICATIONS

Japanese Notice of Allowance for JP2008-238257 issued Jan. 4, 2012.

* cited by examiner

*Primary Examiner* — Hung Dang (57) ABSTRACT

An adjustment device adapted to glasses each including two polarization filters having adjustable transmission axes varying an angle therebetween in a front view is constituted of a physical parameter receiving unit for receiving at least one physical parameter which is produced by measuring the user's body, an angle calculation unit for calculating a target angle to be formed between the transmission axes of the polarization filters based on the received physical parameter, and a polarization filter adjustment unit for rotating at least one of the polarization filters, thus making the present angle formed between the transmission axes of the polarization filters agree with the target angle. Thus, it is possible to reduce a load or strain imparted to a user's eyes in light of the user's fatigued condition.

5 Claims, 5 Drawing Sheets

| USER ID | BLOOD PRESSURE | HEARTBEAT | BREATHING RATE | TEMPERATURE | PERSPIRATION | BODY SURFACE MOISTURE | BRAIN WAVE | ... |
|---|---|---|---|---|---|---|---|---|
| 0001 | | | | | | | | |
| 0002 | | | | | | | | |
| 0003 | | | | | | | | |
| ... | | | | | | | | |

FIG. 5

METHOD AND DEVICE FOR ADJUSTING LUMINANCE OF LIGHT TRANSMITTED THROUGH GLASSES

The present application is based upon and claims priority on Japanese Patent Application No. 2008-238257, the content of which is incorporated herein by reference.

BACKGROUND OF THE INVENTION

1. Field of the Invention

The present invention relates to methods and devices for adjusting luminance (or luminous intensity) of light transmitted through glasses. The present invention also relates to glasses having a capability of adjusting the luminance of light transmitted therethrough. In addition, the present invention relates to programs implementing adjustment of luminance of light transmitted through glasses.

2. Description of the Related Art

Various types of methods and devices for adjusting luminance (i.e. luminous intensity or brightness) of light transmitted through glasses have been developed and disclosed in various documents such as Patent Document 1.

Patent Document 1: Japanese Unexamined Patent Application Publication No. 2008-76767

Patent Document 1 disclose a method for preventing eyestrain (or asthenopia) of users, in which the luminance of a display is adjusted based on the measured illumination in applied environments. This reduces a load or strain to the user's eyes so as to achieve a high visibility in display.

In general, users may frequently experience flickering in the eyes due to accumulated eyestrain due to long periods of watching display screens. The present inventor has recognized that the technology of Patent Document 1 is simply designed to adjust the luminance of a display based on the illumination of applied environments but is not designed in light of fatigued conditions of users.

SUMMARY

The present invention seeks to solve the above problem, or to improve upon the problem at least in part.

The present embodiment aims at reducing a load or strain to a user's eyes based on the user's physical conditions.

Specifically, the present invention is directed to an adjustment device adapted to glasses each including two polarization filters whose transmission axes are adjustable in a front view. The adjustment device includes a physical parameter reception unit for receiving at least one physical parameter which is produced by measuring a user's body; an angle calculation unit for calculating a target angle to be formed between the transmission axes of the polarization filters based on the received physical parameter; and a polarization filter adjustment unit for rotating at least one of the polarization filters, thus making a present angle formed between the transmission axes of the polarization filters agree with the target angle.

The present invention is directed to a glasses including a pair of two polarization filters having adjustable transmission axes varying an angle therebetween in a front view; a physical parameter reception unit for receiving at least one physical parameter which is produced by measuring a user's body; an angle calculation unit for calculating a target angle to be formed between the transmission axes of the polarization filters based on the received physical parameter; and a polarization filter adjustment unit for rotating at least one of the polarization filters, thus making a present angle formed between the transmission axes of the polarization filters agree with the target angle.

The present invention is directed to an adjustment method including the steps of: receiving at least one physical parameter which is produced by measuring a user's body; calculating a target angle to be formed between the transmission axes of the polarization filters based on the received physical parameter; and rotating at least one of the polarization filters, thus making a present angle formed between the transmission axes of the polarization filters agree with the target angle.

The present invention is directed to a program causing a computer to implement a polarization filter adjustment process including the steps of: receiving at least one physical parameter which is produced by measuring a user's body; calculating a target angle to be formed between the transmission axes of the polarization filters based on the received physical parameter; and rotating at least one of the polarization filters, thus making a present angle formed between the transmission axes of the polarization filters agree with the target angle.

BRIEF DESCRIPTION OF THE DRAWINGS

The above features and advantages of the present invention will be more apparent from the following description of certain preferred embodiments taken in conjunction with the accompanying drawings, in which.

DETAILED DESCRIPTION OF PREFERRED EMBODIMENT

The present invention will be now described herein with reference to illustrative embodiments. Those skilled in the art will recognize that many alternative embodiments can be accomplished using the teachings of the present invention and that the invention is not limited to the embodiments illustrated for explanatory purposes.

Figure 1:
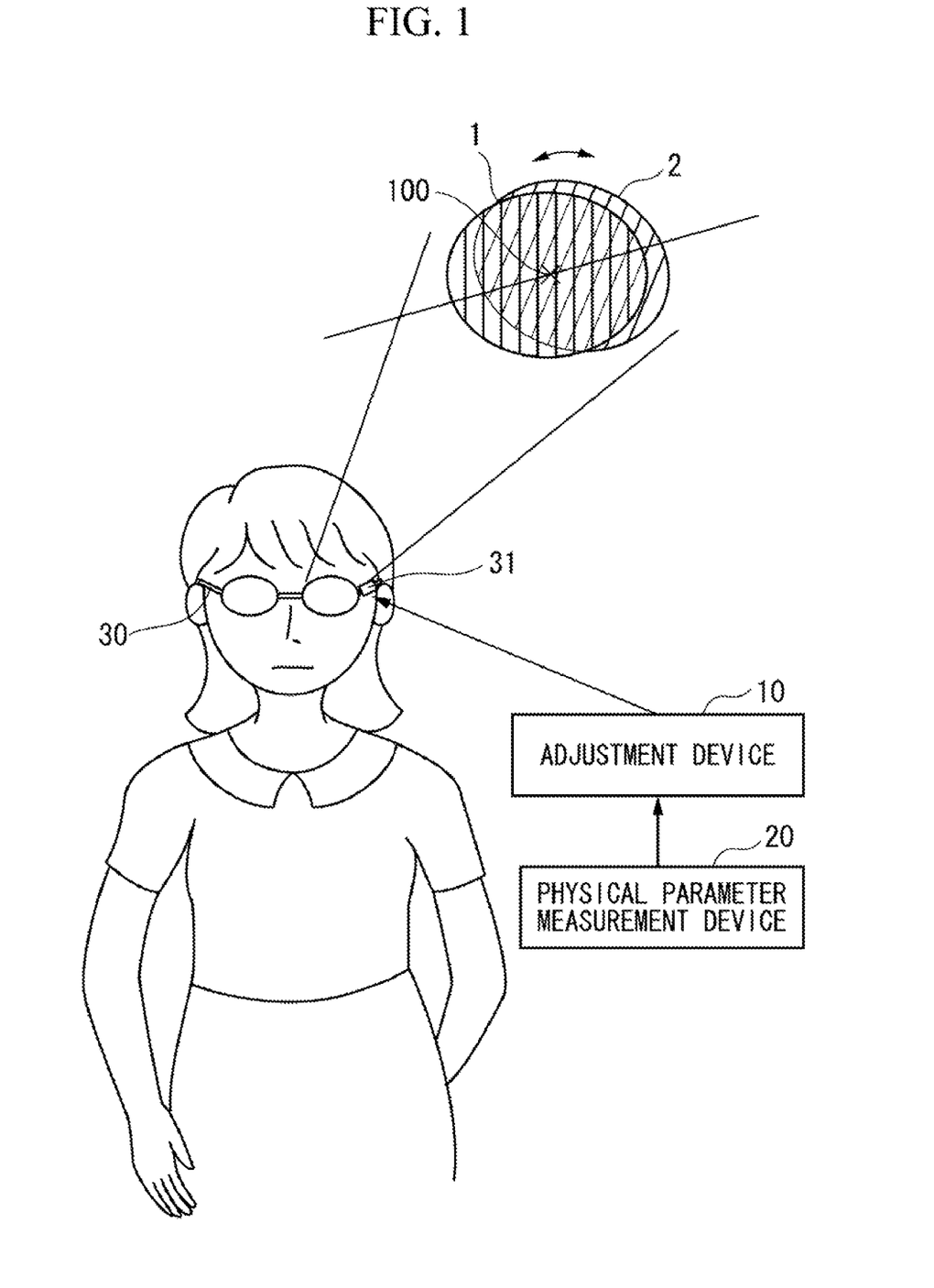
FIG. 1 is an illustration showing a polarization filter adjustment system including an adjustment device and a physical parameter measurement device in connection to glasses worn by a user.

FIG. 1 is an illustration showing the overall constitution of a polarization filter adjustment system according to one embodiment of the present invention.

The polarization filter measurement system includes an adjustment device 10, a physical parameter measurement unit 20, and glasses 30. The adjustment device 10 and the physical parameter measurement unit 20 are connected together so as to communicate with each other. The adjustment device 10 is connected to drive a motor 31.

The physical parameter measurement unit 20 periodically measures physical parameters of a user wearing the glasses 30 in each prescribed time. The physical parameter measurement unit 20 applies a user ID (corresponding to an identification number of each user) to the measured physical parameters, which are transmitted to the adjustment device 10. The present embodiment refers to various physical parameters such as the blood pressure, heartbeat, breathing rate, temperature, perspiration, body surface moisture, and brain waves.

The glasses 30 are eyeglasses whose frame includes a pair of temples having earpieces being hung on the user's ears. Each glass (or each lens) includes a pair of polarization filters 1 and 2, polarizations of which approximately agree to each other in a front view. The polarization filter 1 is fixed to the frame, while the polarization filter 2 is disposed in a rotatable manner about an axis 100. The polarization filters 1 and 2 transmit only the prescribed linear polarized light therethrough. The motor 31 is driven to rotate the polarization filter 2 about the axis 100.

The adjustment device 10 adjusts the rotation angle of the polarization filters 2 attached to the glasses 30 based on physical parameters measured by the physical parameter measurement unit 20. Specifically, the adjustment device 10 transmits an electric signal representative of physical parameters to the motor 31, which is thus driven to rotate the polarization filter 2.

Figure 2:
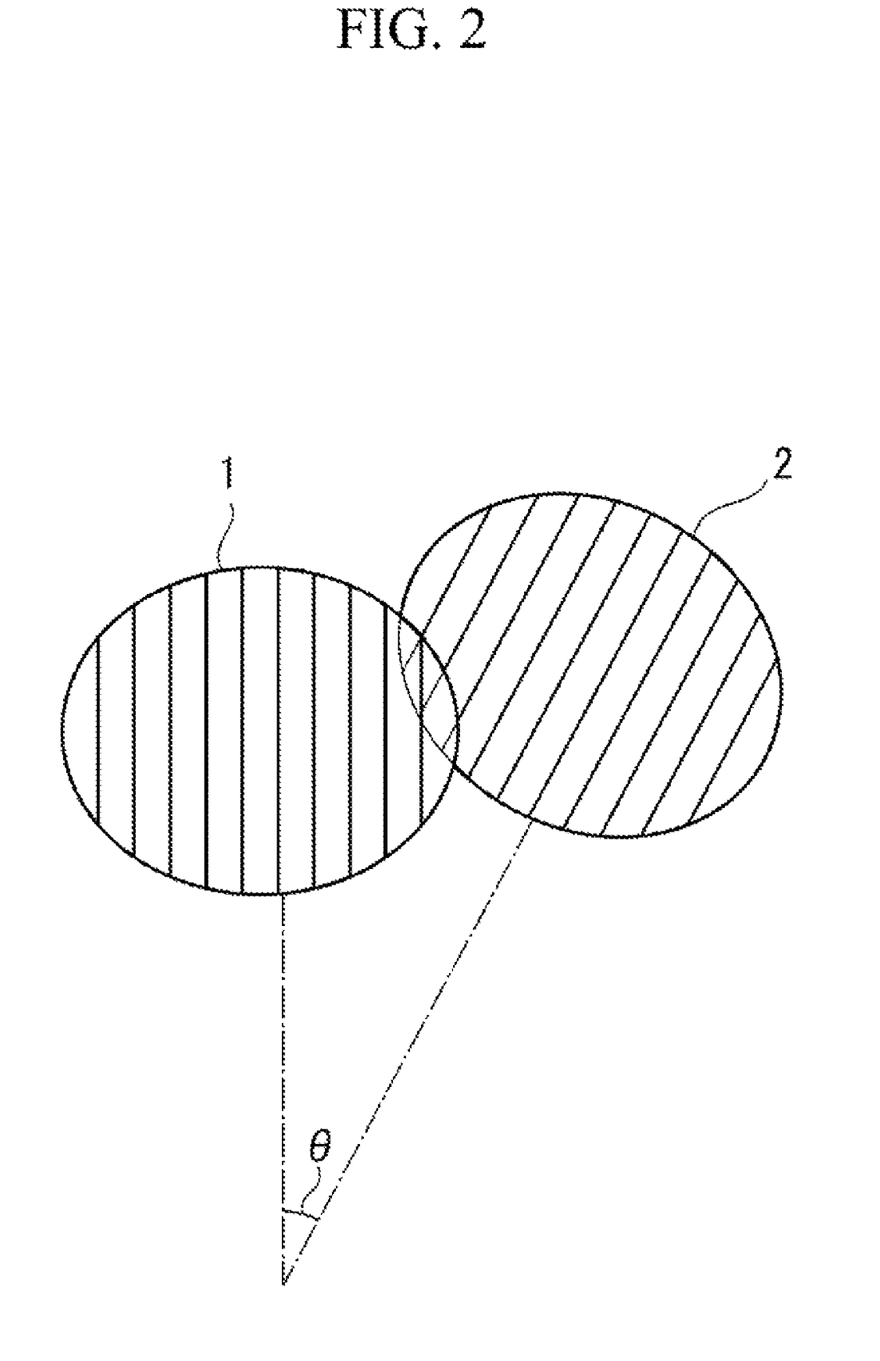
FIG. 2 is an illustration used for explaining the luminance of the light transmitted through each glass including two polarization filters.

FIG. 2 is an illustration used for explaining the luminance (or luminous intensity) of light transmitted through the glasses 30. Vertical lines of the polarization filters 1 and 2 indicate transmission axes of the polarization filters 1 and 2. The transmission axis of the polarization filter 2 is inclined by an angle $\theta$ with respect to the transmission axis of the polarization filter 1. In other words, the angle $\theta$ is formed between the transmission axis of the polarization filter 1 and the transmission axis of the polarization filter 2. It is possible to change the angle $\theta$ in a 0-90 degree range by rotating the polarization filter 2. This changes the angle $\theta$ between the transmission axes of the polarization filters 1 and 2 in a front view. In the case of $\theta=0$ degrees, the transmission axis of the polarization filter 1 agrees with the transmission axis of the polarization filter 2. That is, the polarization direction of the light transmitted through the polarization filter 1 agrees with the polarization direction of the light transmitted through the polarization filter 2. In the case of $\theta=90$ degrees, the transmission axis of the polarization filter 1 is orthogonal to the transmission axis of the polarization filter 2. That is, the polarization direction of the light transmitted through the polarization filter 1 is orthogonal to the polarization direction of the light transmitted through the polarization filter 2. This demonstrates that the luminance of the light transmitted through the glasses 30 increases as the angle $\theta$ approaches 0 degrees, while the luminance of the light transmitted through the glasses 30 decreases as the angle $\theta$ approaches 90 degrees. In this connection, the luminance of the light transmitted through the glasses 30 varies in proportion to $\cos(\theta)$.

Figure 3:
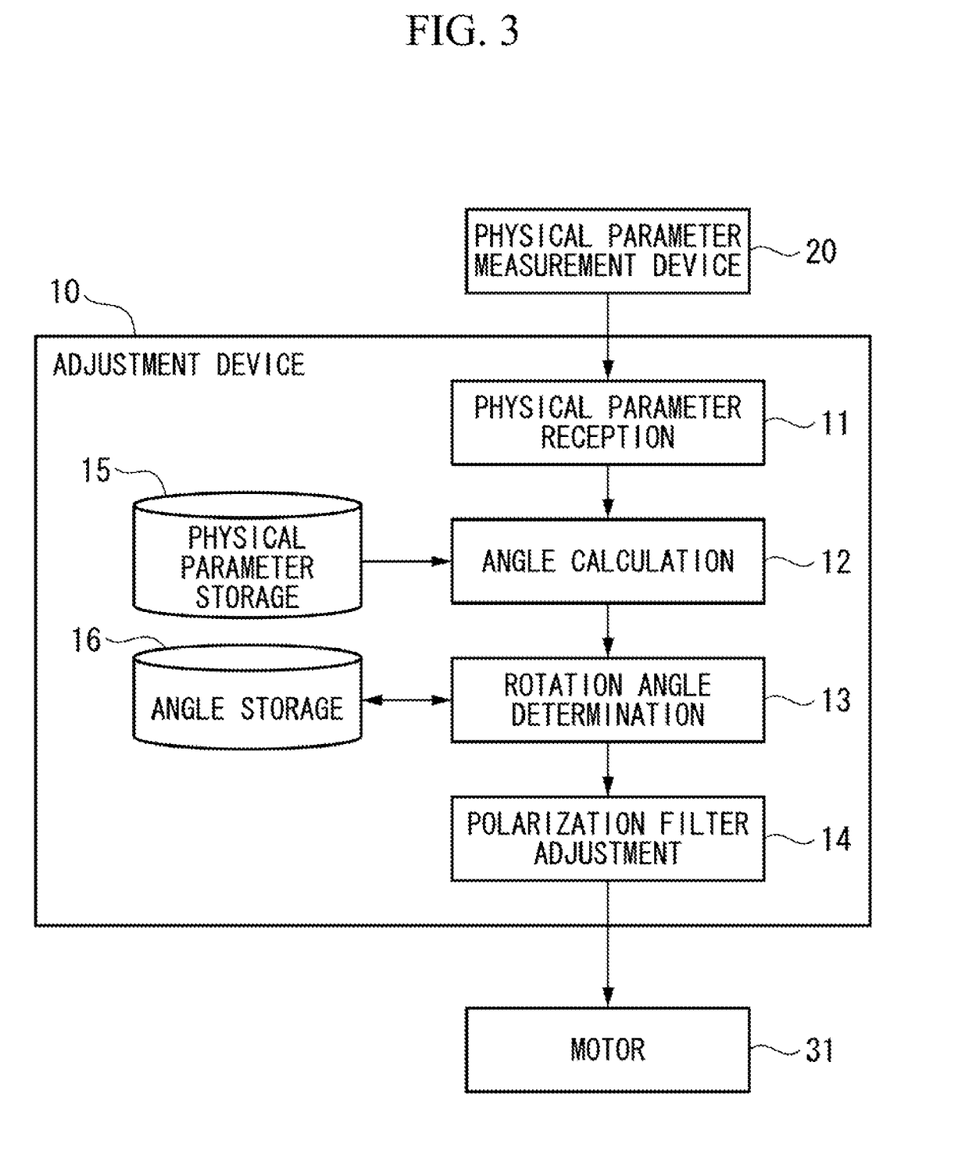
FIG. 3 is a block diagram showing the constitution of the adjustment device that adjusts an angle between transmission axes of polarization filters.

FIG. 3 is a block diagram showing the constitution of the adjustment device 10 according to the present embodiment.

The adjustment device 10 includes a physical parameter reception unit 11, an angle calculation unit 12, a rotation angle determination unit 13, a polarization filter adjustment unit 14, a physical parameter storage unit 15, and a rotation angle storage unit 16.

The physical parameter reception unit 11 receives physical parameters from the physical parameter measurement device 20 and then transmits them to the angle calculation unit 12. Based on the physical parameters received by the physical parameter reception unit 11, the angle calculation unit 12 calculates a target value of the angle $\theta$ (referred to as a target angle $\theta$) to be formed between the transmission axes of the polarization filters 1 and 2; then, the angle calculation unit 12 sends the calculated target angle $\theta$ to the rotation angle determination unit 13. The rotation angle determination unit 13 determines a rotation angle $\beta$ used for rotating the polarization filter 2 based on the target angle $\theta$; then, the rotation angle determination unit 13 sends the rotation angle $\beta$ to the polarization filter adjustment unit 14. The polarization filter adjustment unit 14 drives the motor 31 so as to rotate the polarization filter 2 by the rotation angle $\beta$. The physical parameter storage unit 15 stores physical parameter tables (describing physical parameters) in connection to users. The rotation angle storage unit 16 stores the target angle $\theta$.

Figure 4:
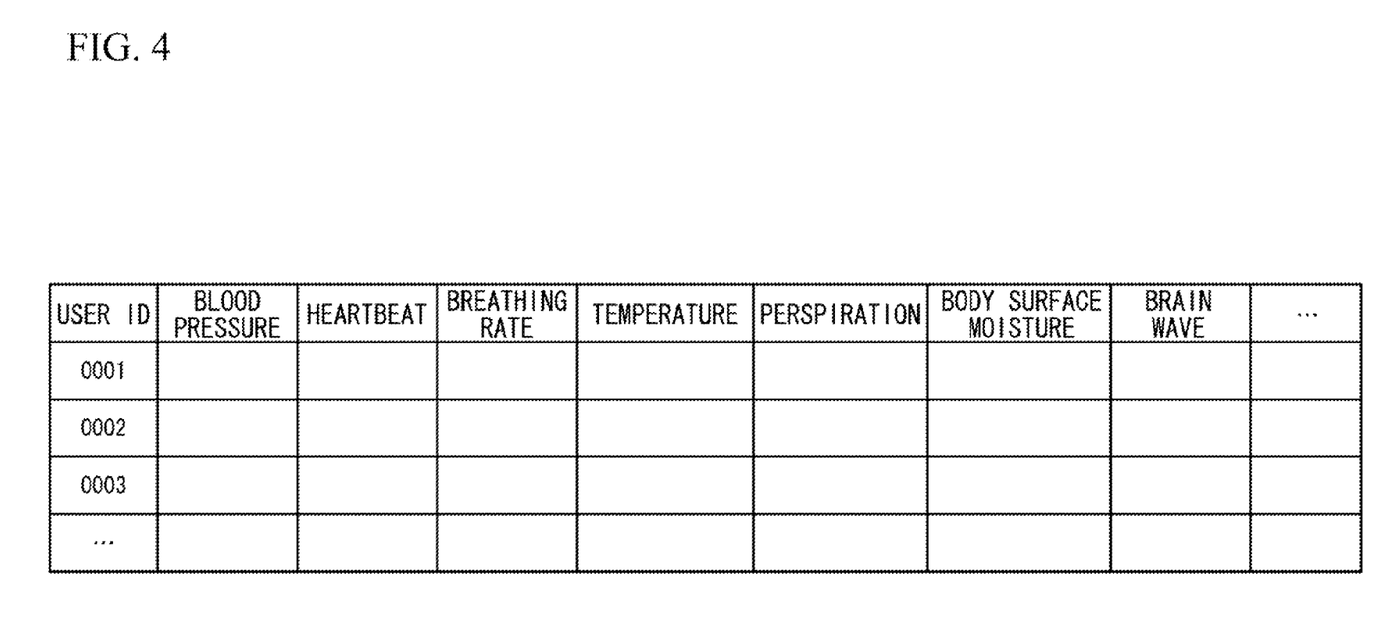
FIG. 4 shows the outline of a physical parameter table describing physical parameters in connection to each user.

FIG. 4 shows the outline of a physical parameter table describing physical parameters in connection to users.

The physical parameter table is a two-dimensional table consisting of rows and columns, describing various data in relation to various items representing the user ID, blood pressure, heartbeat, breathing rate, temperature, perspiration, body surface moisture, and brain waves. The main key accessing the physical parameter table is the user ID which is an identification number univocally identifying a specific user. The items of the blood pressure, heartbeat, breathing rate, temperature, perspiration, body surface moisture, and brain waves are physical parameters.

Figure 5:
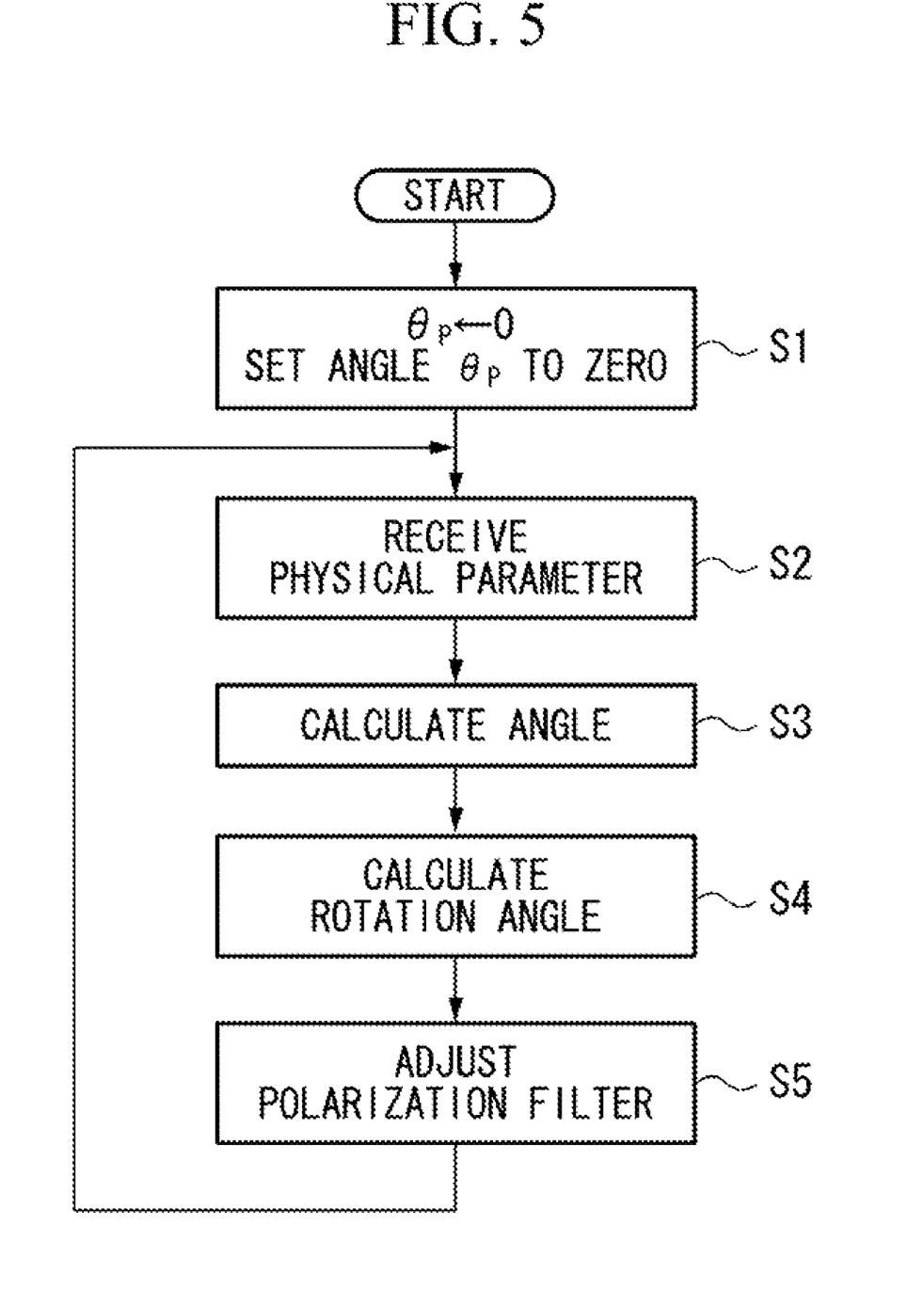
FIG. 5 is a flowchart showing a polarization filter adjustment process for adjusting the angle between the transmission axes of the polarization filters.

FIG. 5 is a flowchart showing a polarization filter adjustment process implemented by the adjustment device 10. The following description refers to only the item of the blood pressure in the physical parameter table.

In step S1, the angle calculation unit 12 sets a present angle $\theta_P$ to 0 degrees, which is stored in the rotation angle storage unit 16. At this time, the polarization filter adjustment unit 14 drives the motor 31 to initialize the angle (i.e. zero degree) between the transmission axes of the polarization filters 1 and 2.

In step S2, the physical parameter reception unit 11 receives a blood pressure $B_1$ and its user ID from the physical parameter measurement unit 20, and then sends them to the angle calculation unit 12.

In step S3, the angle calculation unit 12 calculates the target angle $\theta$ to be formed between the transmission axes of the polarization filters 1 and 2 based on the blood pressure $B_1$. Specifically, the angle calculation unit 12 reads a blood pressure $A_1$ connected to the user ID from the physical parameter table; then, the angle calculation unit 12 calculates the target angle $\theta$ in accordance with Equation (1). Equation (1) indicates that, as the blood pressure B1 increases, the target angle $\theta$ decreases, that is, the luminance of the light transmitted through the glasses 30 increases. Equation (1) also indicates that, as the blood pressure $B_1$ decreases, the target angle $\theta$ increases, that is, the luminance of the light transmitted through the glasses 30 decreases. In Equation (1), c1 denotes a positive constant, and $\alpha$ (where $0<\alpha<90$) denotes a reference angle which is determined in advance.

$$\theta = \frac{A_1}{B_1} \times c1 \times \alpha \quad (1)$$

$$\text{if}\left(\frac{A_1}{B_1} \times c1 \times \alpha < 90\right)$$

$$\theta = 90$$

$$\text{if}\left(\frac{A_1}{B_1} \times c1 \times \alpha \geq 90\right)$$

In step S4, the rotation angle determination unit 13 determines the rotation angle $\beta$ applied to the polarization filter 2. The rotation angle determination unit 13 reads the present angle $\theta_P$ from the rotation angle storage unit 16, and then the rotation angle determination unit 13 subtracts the present angle $\theta_P$ from the target angle $\theta$ so as to determine the rotation angle $\beta$. In addition, the rotation angle determination unit 13 stores the target angle $\theta$ as the present angle in the rotation angle storage unit 16.

In step S5, the polarization filter adjustment unit 14 drives the motor 31 so as to rotate the polarization filter 2 by the rotation angle $\beta$; then, the processing reverts to step S2. Specifically, the polarization filter adjustment unit 14 sends an electric signal representative of the rotation angle $\beta$ to the motor 31, which is thus driven to rotate the polarization filter 2 by the rotation angle $\beta$. In short, the polarization filter adjustment unit 14 controls the rotation of either the polarization filter 1 or the polarization filter 2 such that the target angle $\theta$ (calculated by the angle calculation unit 12) agrees with the present angle $\theta_P$ formed between the transmission axes of the polarization filters 1 and 2.

As described above, the present embodiment is designed to vary the angle formed between the transmission axes of two polarization filters based on user's physical parameters. Varying the angle between the transmission axes of the polarization filters 1 and 2 attached to each glass 30 leads to varying the luminance of the light reaching the user's eye through each glass 30. That is, the present embodiment allows the user's eyes to receive the optimum luminance of light specifically suited to each user's fatigued condition, thus markedly reducing the load or strain imparted to the user's eyes.

The present embodiment refers to the operation of the adjustment device 10 determining the target angle $\theta$ based on the blood pressure, whereas it is possible to determine the target angle $\theta$ based on the other physical parameter(s).

The following description refers to the operation of the adjustment device 10 determining the target angle $\theta$ based on the heartbeat in accordance with Equation (2). Herein, $B_2$ denotes the heartbeat measured by the physical parameter measuring device 20; $A_2$ denotes the heartbeat registered with the physical parameter table; and c2 denotes a positive constant.

$$\theta = \frac{A_2}{B_2} \times c2 \times \alpha \qquad (2)$$

$$\text{if } \left(\frac{A_2}{B_2} \times c2 \times \alpha < 90\right)$$

$$\theta = 90$$

$$\text{if } \left(\frac{A_2}{B_2} \times c2 \times \alpha \geq 90\right)$$

The following description refers to the operation of the adjustment device 10 determining the target angle $\theta$ based on the breathing rate in accordance with Equation (3). Herein, $B_3$ denotes the breathing rate measured by the physical parameter measurement device 10; $A_3$ denotes the breathing rate registered with the physical parameter table; and c3 denotes a positive constant.

$$\theta = \frac{A_3}{B_3} \times c3 \times \alpha \qquad (3)$$

$$\text{if } \left(\frac{A_3}{B_3} \times c3 \times \alpha < 90\right)$$

$$\theta = 90$$

$$\text{if } \left(\frac{A_3}{B_3} \times c3 \times \alpha \geq 90\right)$$

The following description refers to the operation of the adjustment device 10 determining the target angle $\theta$ based on the body temperature in accordance with Equation (4). Herein, $B_4$ denotes the body temperature measured by the physical parameter measurement device 20; $A_4$ denotes the body temperature registered with the physical parameter table; and c4 denotes a positive constant.

$$\theta = \frac{A_4}{B_4} \times c4 \times \alpha \qquad (4)$$

$$\text{if } \left(\frac{A_4}{B_4} \times c4 \times \alpha < 90\right)$$

$$\theta = 90$$

$$\text{if } \left(\frac{A_4}{B_4} \times c4 \times \alpha \geq 90\right)$$

The following description refers to the operation of the adjustment device 10 determining the target angle $\theta$ based on the perspiration in accordance with Equation (5). Herein, $B_5$ denotes the perspiration measured by the physical parameter measurement device 20; $A_5$ denotes the perspiration registered with the physical parameter table; and c5 denotes a positive constant.

$$\theta = \frac{A_5}{B_5} \times c5 \times \alpha \qquad (5)$$

$$\text{if } \left(\frac{A_5}{B_5} \times c5 \times \alpha < 90\right)$$

$$\theta = 90$$

$$\text{if } \left(\frac{A_5}{B_5} \times c5 \times \alpha \geq 90\right)$$

The following description refers to the operation of the adjustment device 10 determining the target angle $\theta$ based on the body surface moisture in accordance with Equation (6). Herein, $B_6$ denotes the body surface moisture measured by the physical parameter measurement device 20; $A_6$ denotes the body surface moisture registered with the physical parameter table; and c6 denotes a positive constant.

$$\theta = \frac{A_6}{B_6} \times c6 \times \alpha \qquad (6)$$

$$\text{if } \left(\frac{A_6}{B_6} \times c6 \times \alpha < 90\right)$$

$$\theta = 90$$

$$\text{if } \left(\frac{A_6}{B_6} \times c6 \times \alpha \geq 90\right)$$

The following description refers to the operation of the adjustment device 10 determining the target angle $\theta$ based on the brain waves in accordance with Equation (7). Herein, $B_7$ denotes the brain waves measured by the physical parameter measurement device 20; $A_7$ denotes the brain waves registered with the physical parameter table; and c7 denotes a positive constant.

$$\theta = \frac{A_7}{B_7} \times c7 \times \alpha \quad (7)$$

$$\text{if } \left(\frac{A_7}{B_7} \times c7 \times \alpha < 90\right)$$

$$\theta = 90$$

$$\text{if } \left(\frac{A_7}{B_7} \times c7 \times \alpha \geq 90\right)$$

It is possible to store a program representing the procedures of FIG. 5 in computer-readable storage media, thus allowing a computer system to load the program and to execute the polarization filter adjustment process. Herein, the term "computer system" may embrace the operating system (OS) as well as the hardware and peripheral devices.

When the computer system is designed to comply with the World Wide Web (WWW) system, it may embrace networking environments for controlling display images and homepages.

The term "computer-readable media" refers to reloadable (or rewritable) nonvolatile memories such as flexible disks, magneto-optical disks, read-only memories (ROM), and flash memories, portable (or handheld) media such as CD-ROM, and storage units such as hard-disk units installed in computer systems.

In addition, the "computer-readable media" may embrace any other means temporarily holding programs, such as internal volatile memories of computer systems (e.g. DRAM) serving as servers and/or clients adapted to programs transmitted via telephone lines, communication lines, and networks such as the Internet.

Programs may be transferred from the computer system temporarily holding them to the other computer system via transmission media or via media propagating carrier waves. In this connection, the term "transmission media (for transferring programs)" refers to media such as telephones lines, communication lines, and networks (e.g. the Internet) having capabilities of transferring information from one place to another.

It is possible to create a program achieving only a part of the polarization filter adjustment process. Alternatively, it is possible to create a program representing a difference file (or a difference program) supplementing the pre-installed program (representing some of functions of the polarization filter adjustment process) of the computer system.

The present invention is not necessarily limited to the present embodiment, which can be modified in various ways as follows:

(1) The present embodiment is designed to isolate the adjustment device 10 from the glasses 30; but this is not a restriction. It is possible to redesign the glasses 30 incorporating the function of the adjustment device 10.

(2) Alternatively, it is possible to redesign the glasses 30 incorporating the function of the polarization filter adjustment unit 14 of the adjustment device 10, so that the glasses 30 are connected to communicate with the adjustment device 10. Herein, the adjustment device 10 determines and sends the rotation angle β to the glasses 30. That is, the polarization filter adjustment device 14 incorporated in the glasses 30 sends an electric signal designating the received rotation angle β to the motor 31, thus rotating the polarization filter 2 by the rotation angle β.

(3) The present embodiment is designed such that the adjustment device 10 determines the target angle θ based on a single physical parameter, whereas the adjustment device 10 is redesigned to determine the target angle θ based on the combination of plural physical parameters in accordance with Equation (8). Herein, Wi denotes a weight of each physical parameter; and n denotes the number of physical parameters.

$$\theta = \alpha \sum_{i=1}^{n} W_i \left(\frac{A_i}{B_i}\right) \quad (8)$$

As described above, the present invention is designed to change the angle formed between the transmission axes of the polarization filters included in each of glasses based on the user's physical parameter(s). The luminance of light transmitted through each glass is varied when the angle between the transmission axes of the polarization filters is changed by rotating at least one of the polarization filters overlapping with each other. This allows the glasses to arbitrarily adjust the luminance of light reaching the user's eyes in light of the fatigued condition regarding the user's eyes, thus reducing the load or strain imparted to the user's eyes.

It is apparent that the present invention is not limited to the present embodiment and its variations, but may be modified and changed without departing from the scope and spirit of the invention.

What is claimed is:

1. An adjustment device adapted to glasses each including two polarization filters whose transmission axes are adjustable in a front view, comprising:
   a physical parameter reception unit for receiving at least one physical parameter which is produced by measuring a user's body;
   an angle calculation unit for calculating a target angle to be formed between the transmission axes of the polarization filters based on the received physical parameter; and
   a polarization filter adjustment unit for rotating at least one of the polarization filters, thus making a present angle formed between the transmission axes of the polarization filters agree with the target angle.

2. The adjustment device according to claim 1 further comprising a physical parameter storage unit for registering at least one physical parameter with respect to each user, wherein the physical parameter reception unit acquires a user identification assigned to each user so as to read the registered physical parameter from the physical parameter storage unit, so that the angle calculation unit calculates the target angle based on the received physical parameter and the registered physical parameter in connection to the user identification.

3. Glasses comprising:
   a pair of two polarization filters having adjustable transmission axes varying an angle therebetween in a front view;
   a physical parameter reception unit for receiving at least one physical parameter which is produced by measuring a user's body;
   an angle calculation unit for calculating a target angle to be formed between the transmission axes of the polarization filters based on the received physical parameter; and
   a polarization filter adjustment unit for rotating at least one of the polarization filters, thus making a present angle formed between the transmission axes of the polarization filters agree with the target angle.

4. An adjustment method adapted to glasses each including two polarization filters whose transmission axes are adjustable in a front view, comprising:
   receiving at least one physical parameter which is produced by measuring a user's body;
   calculating a target angle to be formed between the transmission axes of the polarization filters based on the received physical parameter; and
   rotating at least one of the polarization filters, thus making a present angle formed between the transmission axes of the polarization filters agree with the target angle.

5. A program causing a computer to implement a polarization filter adjustment process adapted to glasses each including two polarization filters whose transmission axes are adjustable in a front view, comprising:
   receiving at least one physical parameter which is produced by measuring a user's body;
   calculating a target angle to be formed between the transmission axes of the polarization filters based on the received physical parameter; and
   rotating at least one of the polarization filters, thus making a present angle formed between the transmission axes of the polarization filters agree with the target angle.

* * * * *